United States Patent
Brannan et al.

(10) Patent No.: US 11,369,434 B2
(45) Date of Patent: Jun. 28, 2022

(54) SYSTEMS AND METHODS FOR DETERMINING THE STATUS OF A FLUID-COOLED MICROWAVE ABLATION SYSTEM

(71) Applicant: COVIDIEN LP, Mansfield, MA (US)

(72) Inventors: Joseph D. Brannan, Lyons, CO (US); Robert J. Behnke, II, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 757 days.

(21) Appl. No.: 15/189,716

(22) Filed: Jun. 22, 2016

(65) Prior Publication Data
US 2017/0367759 A1    Dec. 28, 2017

(51) Int. Cl.
*A61B 18/18*    (2006.01)
*A61M 1/00*    (2006.01)
(Continued)

(52) U.S. Cl.
CPC ...... *A61B 18/1815* (2013.01); *A61B 2018/00023* (2013.01); *A61B 2018/00577* (2013.01);
(Continued)

(58) Field of Classification Search
CPC ...... A61B 18/1815; A61B 2018/00005; A61B 2018/00023; A61B 2018/00577;
(Continued)

(56) References Cited

U.S. PATENT DOCUMENTS 5,739,508 A * 4/1998 Uber, III ............... A61M 5/172
235/383
6,440,128 B1 * 8/2002 Edwards ............ A61B 18/1485
606/41
(Continued)

FOREIGN PATENT DOCUMENTS

| AU | 2007201161 A1 | 4/2007 |
|---|---|---|
| CN | 103442631 A | 12/2013 |
| CN | 104042340 A | 9/2014 |
| JP | 2016-515441 A | 5/2016 |
| WO | 00/66015 A1 | 11/2000 |
| WO | 2015089377 A1 | 6/2015 |

OTHER PUBLICATIONS

Extended European Search Report for application No. 17177206.4 dated Nov. 2, 2017.
U.S. Appl. No. 62/154,924, filed Apr. 30, 2015, entitled "Methods for Microwave Ablation Planning and Procedure" to Girotto.
Japanese Office Action for application No. 2017-119436 dated Mar. 29, 2018 with English Translation.
(Continued)

*Primary Examiner* — Joanne M Hoffman
*Assistant Examiner* — Rachel A. Vierra
(74) *Attorney, Agent, or Firm* — Carter, DeLuca & Farrell LLP (57) ABSTRACT

A method of determining the status of a fluid cooled microwave ablation system is provided including providing an electrical current to a pump to pump fluid through an ablation system along a fluid path to cool the ablation system, measuring an electrical current drawn by the pump, and determining a status of the ablation system based on the measured electrical current. In another aspect of the disclosure, an ablation system is provided including an ablation probe defining a fluid path for circulation of fluid therethrough, a generator configured to supply energy to the ablation probe for treating tissue, a pump configured to pump fluid through the fluid path of the ablation probe to cool the ablation probe, a sensor configured to measure an electrical current drawn by the pump, and a computing device configured to determine a status of the ablation system based on the measured electrical current.

19 Claims, 6 Drawing Sheets

(51) Int. Cl.
   *A61B 18/00* (2006.01)
   *A61M 5/168* (2006.01)
(52) U.S. Cl.
   CPC .............. *A61B 2018/00642* (2013.01); *A61B 2018/00666* (2013.01); *A61B 2018/00702* (2013.01); *A61B 2018/00708* (2013.01); *A61B 2018/00744* (2013.01); *A61B 2018/00827* (2013.01); *A61B 2018/00898* (2013.01); *A61B 2018/1823* (2013.01); *A61M 1/00* (2013.01); *A61M 5/16831* (2013.01); *A61M 5/16854* (2013.01); *A61M 5/16877* (2013.01); *A61M 2005/16863* (2013.01); *A61M 2205/15* (2013.01)
(58) Field of Classification Search
   CPC ........... A61B 2018/00702; A61B 2018/00744; A61B 2018/00827; A61B 2018/00898; A61B 2018/1823; A61M 5/16877; A61M 5/16831; A61M 5/16854; A61M 1/00; A61M 2005/16862; A61M 2205/15
   See application file for complete search history.

(56) References Cited

U.S. PATENT DOCUMENTS

| 8,292,881 | B2 | 10/2012 | Brannan et al. |
| 9,119,650 | B2 | 9/2015 | Brannan et al. |
| 9,247,992 | B2 | 2/2016 | Ladtkow et al. |
| 2004/0085215 | A1* | 5/2004 | Moberg ............ A61M 5/16854 340/679 |
| 2009/0221999 | A1 | 9/2009 | Shahidi |
| 2009/0222002 | A1 | 9/2009 | Bonn et al. |
| 2011/0060326 | A1 | 3/2011 | Smith et al. |
| 2011/0077637 | A1 | 3/2011 | Brannan |
| 2011/0077639 | A1 | 3/2011 | Brannan et al. |
| 2011/0295245 | A1* | 12/2011 | Willyard ............ A61B 18/1815 606/33 |
| 2013/0267779 | A1 | 10/2013 | Woolford et al. |
| 2014/0259641 | A1* | 9/2014 | Brannan ............ A61B 18/1815 29/602.1 |
| 2015/0320478 | A1 | 11/2015 | Cosman, Jr. et al. |
| 2016/0058507 | A1 | 3/2016 | Dickhans |
| 2017/0000959 | A1* | 1/2017 | Mantell ............ A61B 17/3474 |

OTHER PUBLICATIONS

Canadian Office Action for application No. 2,968,749 dated Feb. 23, 2018 (5 pages).
Australian Examination Report for application No. 2017203533 dated Mar. 14, 2018 (3 pages).
Japanese Office Action issued in Appl. No. JP 2017-119436 dated Oct. 26, 2018, together with English language translation (9 pages).
Canadian Office Action issued in corresponding Appl. No. CA 2,968,749 dated Nov. 26, 2018 (4 pages).
Office Action issued in corresponding Appl. No. CN 201710472179.4 dated Aug. 12, 2019 (8 pages).

* cited by examiner

SYSTEMS AND METHODS FOR DETERMINING THE STATUS OF A FLUID-COOLED MICROWAVE ABLATION SYSTEM

BACKGROUND

1. Technical Field

The present disclosure relates to microwave ablation systems and methods and, more particularly, to systems and methods for determining the status of a fluid cooled microwave ablation system.

2. Discussion of Related Art

Treatment of certain diseases requires the destruction of malignant tissue growths, e.g., tumors. Electromagnetic ("EM") radiation can be used to heat and destroy tumor cells. Treatment may involve inserting ablation probes into or adjacent to tissues where cancerous tumors have been identified. Once the probes are positioned, electromagnetic energy is passed through the probes into surrounding tissue to treat, e.g., heat, ablate and/or coagulate tissue.

EM ablation probes may require cooling to operate within desired parameters without damaging the ablation device or causing unintended tissue damage. Some probes implement cooling systems including a peristaltic pump that circulates a cooling fluid through a tubing system and the ablation probe, such that heat is drawn away from the ablation probe. Cooling the ablation probe may enhance the overall ablation pattern, prevent damage to the probe, and prevent harm to the clinician or patient.

However, during operation, if the flow of cooling fluid is interrupted or becomes irregular, the ablation probe may exhibit failure or reduced performance.

SUMMARY

Provided in accordance with aspects of the present disclosure is a method of determining the status of a fluid cooled microwave ablation system. The method includes providing an electrical current to a pump to pump fluid through an ablation system along a fluid path to cool the ablation system, measuring an electrical current drawn by the pump, and determining a status of the ablation system based on the measured electrical current.

In an aspect of the present disclosure, determining the status of the ablation system includes determining whether the measured electrical current is within a predetermined range.

In another aspect of the present disclosure, if the measured electrical current is outside the predetermined range, operation of the ablation system is adjusted.

In yet another aspect of the present disclosure, adjusting operation of the ablation system includes inhibiting the pumping of fluid through the ablation system.

In still another aspect of the present disclosure, adjusting operation of the ablation system includes inhibiting supplying of energy to the ablation system.

In still yet another aspect of the present disclosure, if the measured electrical current is outside the predetermined range, an alert is provided.

In another aspect of the present disclosure, the alert is displayed on a display screen.

In yet another aspect of the present disclosure, the electrical current is displayed on the display screen.

In still another aspect of the present disclosure, the determining the status includes determining whether the ablation system is functioning normally or abnormally.

In still yet another aspect of the present disclosure, determining that the ablation system is functioning abnormally indicates at least one of a blockage or a leakage in the ablation system.

Provided in accordance with another aspect of the present disclosure is an ablation system including an ablation probe defining a fluid path for circulation of fluid therethrough, a generator configured to supply energy to the ablation probe for treating tissue, a pump configured to pump fluid through the fluid path of the ablation probe to cool the ablation probe, a sensor configured to measure an electrical current drawn by the pump, and a computing device configured to determine a status of the ablation system based on the measured electrical current.

In another aspect of the present disclosure, the computing device is configured to determine the status of the ablation system by determining whether the measured electrical current is within a predetermined range.

In still another aspect of the present disclosure, the computing device is further configured, if the measured electrical current is outside the predetermined range, to inhibit the pump from pumping of fluid through the ablation probe.

In still yet another aspect of the present disclosure, the computing device is further configured, if the measured electrical current is outside the predetermined range, to inhibit the supply of energy from the generator to the ablation probe.

In another aspect of the present disclosure, the computing device is further configured, if the measured electrical current is outside the predetermined range, to provide an alert.

In yet another aspect of the present disclosure, a display screen is configured to display the alert.

In still another aspect of the present disclosure, the display screen is further configured to display the measured electrical current.

In still yet another aspect of the present disclosure, in determining the status, the computing device is configured to determine whether the ablation system is functioning normally or abnormally.

In another aspect of the present disclosure, a determination by the computing device that the ablation system is functioning abnormally indicates at least one of a blockage or a leakage in the ablation system.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

Measuring parameters of a pump used to circulate fluid through a fluid cooled microwave ablation assembly can be useful in determining the status of the cooling system. Specifically, the electrical current drawn by the pump can provide useful information, e.g., how much fluid is being used, the condition of components in the system, an assessment of energy being delivered by the fluid cooled microwave ablation antenna assembly, and/or whether or not the cooling system is operating within established parameters. These and other aspects and features of the present disclosure are detailed herein below.

Figure 1:
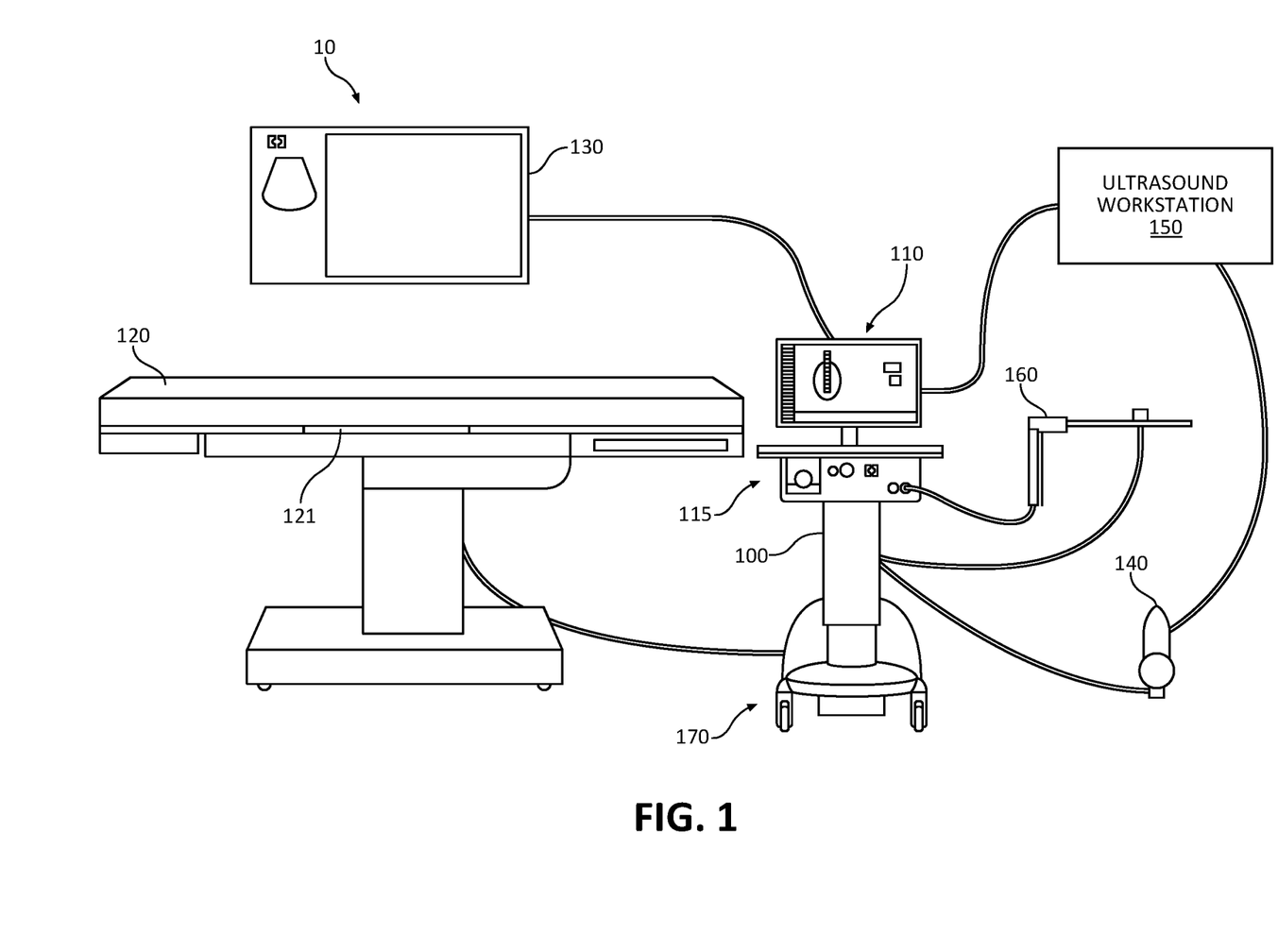
FIG. 1 is a side view of a fluid cooled microwave ablation system provided in accordance with the present disclosure.

Referring now to FIG. 1, an exemplary fluid cooled microwave ablation system 10 of the present disclosure is depicted. The microwave ablation system 10 includes a computing device 100 storing one or more ablation planning and electromagnetic tracking applications, a touch display computer 110 which is an integrated computing device and display system controlling microwave ablation generator 115 via one or more user interfaces and a touch sensitive screen, an operating table 120, including an electromagnetic (EM) field generator 121, a second display 130, an ultrasound imaging sensor 140, an ultrasound workstation 150, a fluid cooled microwave ablation antenna assembly 160, and a base unit 170 configured to support computing device 100, the microwave ablation generator 115 the touch display computer 110, and the antenna assembly 160. Computing devices described herein may be, for example, a laptop computer, desktop computer, tablet computer, or other similar device. Touch display computer 110 is configured to control microwave generator 115 (see FIG. 3), pump 117 (see FIG. 3) and other accessories and peripheral devices relating to, or forming part of, fluid cooled microwave ablation system 10. Touch display computer 110 is configured to present a user interface enabling a clinician to input instructions and setting for the microwave ablation generator 115, display images, and/or messages relating to the performance of the microwave ablation generator 115, the progress of a procedure, and issue alarms or alerts related to the same.

Operating table 120 may be any table suitable for use during a surgical procedure, which in certain embodiments includes or is associated with an EM field generator 121. EM field generator 121 is used to generate an EM field during the microwave ablation procedure and forms part of an EM tracking system, which is used to track the positions of surgical instruments, e.g., microwave ablation antenna assembly 160 and ultrasound sensor 140, within the EM field around and within the body of a patient. Second display 130 (FIG. 1), in association with computing device 100, may be used for displaying ultrasound imaging and providing visualization of tissue to be treated as well as navigation of the fluid cooled microwave ablation antenna assembly 160. However, it is envisioned that touch display computer 110 and computing device 100 may also be used for ultrasound imaging and navigation purposes in addition to its microwave ablation generator 115 control functions discussed above.

As will be described in more detail below (FIGS. 3 and 4), microwave ablation antenna assembly 160 is used to ablate tissue, e.g., a lesion or tumor (hereinafter referred to as a "target"), by using microwave energy to heat tissue in order to denature or kill cancerous cells. Further, although an exemplary microwave ablation antenna assembly 160 is detailed herein, it is contemplated that other suitable microwave ablation probes may be utilized in accordance with the present disclosure. For example, the ablation probes and systems described in U.S. patent application Ser. No. 14/828,682 entitled MICROWAVE ABLATION SYSTEM, filed on Aug. 18, 2015 by Dickhans, International Application No. PCT/US15/46729 entitled MICROWAVE ABLATION SYSTEM, filed on Aug. 25, 2015 by Dickhans, U.S. patent application Ser. No. 13/836,203 entitled MICROWAVE ABLATION CATHETER AND METHOD OF UTILIZING THE SAME, filed on Mar. 15, 2013 by Ladtkow et al., and U.S. patent application Ser. No. 13/834,581 entitled MICROWAVE ENERGY-DELIVERY DEVICE AND SYSTEM, filed on Mar. 15, 2013 by Brannan et al., the entire contents of each of which are incorporated herein by reference, may be used in conjunction with the aspects and features of the present disclosure.

In addition to the EM tracking system, the surgical instruments, e.g., microwave ablation antenna assembly 160, may also be visualized by using ultrasound imaging work station 150. Ultrasound sensor 140, such as an ultrasound wand, may be used to image the patient's body during the microwave ablation procedure to visualize the location of microwave ablation antenna assembly 160 inside the patient's body. Ultrasound sensor 140 may have an EM tracking sensor embedded within or attached to the ultrasound wand, for example, a clip-on sensor or a sticker sensor. Ultrasound sensor 140 may be positioned in relation to microwave ablation antenna assembly 160 such that microwave ablation antenna assembly 160 is at an angle to the ultrasound image plane, thereby enabling the clinician to visualize the spatial relationship of microwave ablation antenna assembly 160 with the ultrasound image plane and with objects being imaged. Further, the EM tracking system may also track the location of ultrasound sensor 140. This spatial depiction of the ultrasound sensor 140 and the microwave ablation antenna assembly 160 is described in greater detail in U.S. patent application Ser. No. 62/154,924 entitled METHODS FOR MICROWAVE ABLATION PLANNING AND PROCEDURE, filed on Apr. 30, 2015 by Girotto which is incorporated herein by reference. During surgery, one or more ultrasound sensors 140 may be placed on or inside the body of the patient. EM tracking system may then track the location of such ultrasound sensors 140 and microwave ablation antenna assembly 160 as they are moved relative to each other.

Figure 2:
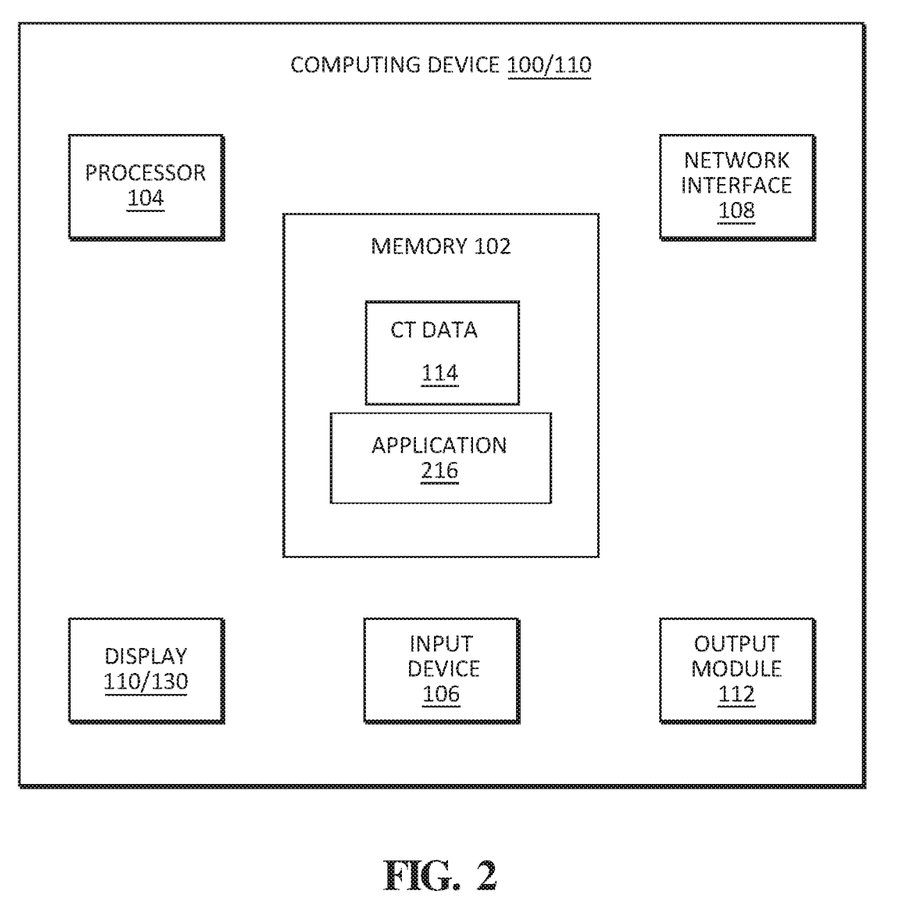
FIG. 2 is a schematic diagram of a computing device of the fluid cooled microwave ablation system of FIG. 1.

Turning now to FIG. 2, a system diagram of computing device 100 and touch display computer 110 of system 10 are generally depicted. Computing device 100 and touch display computer 110 may include memory 102, processor 104, display 130 or 110, network interface 108, input device 106, and/or output module 112. Memory 102 includes any non-transitory computer-readable storage media for storing data and/or software that is executable by processor 104 and which controls the operation of computing device 100. Processor 104 may be a general purpose processor, a specialized graphics processing unit (GPU) configured to perform specific graphics processing tasks while freeing up the general purpose processor to perform other tasks, and/or any number or combination of such processors. As noted above with respect to touch display computer 110, display 130 or 110 may be touch sensitive and/or voice activated, enabling display 130 or 110 to serve as both an input and output device. Alternatively, a keyboard (not shown), mouse (not shown), or other data input devices may be employed.

Network interface 108 may be configured to connect to a network such as a local area network (LAN) consisting of a wired network and/or a wireless network, a wide area network (WAN), a wireless mobile network, a Bluetooth network, and/or the internet. For example, computing device 100 or and touch display computer 110 may receive computed tomographic (CT) image data of a patient from a server, for example, a hospital server, internet server, or other similar servers, for use during surgical ablation planning. Patient CT image data 114 may also be provided to computing device 100 and touch display computer 110 via memory 102. Computing device 100 may receive updates to its software, for example, application 216, via network interface 108. Computing device 100 may also display notifications on display 130 or 110 that a software update is available. Input device 106 may be any device by means of which a user may interact with computing device 100 or and touch display computer 110, such as, for example, a mouse, keyboard, foot pedal, touch screen, and/or voice interface. Output module 112 may include any connectivity port or bus, such as, for example, parallel ports, serial ports, universal serial busses (USB), or any other similar connectivity port known to those skilled in the art.

Figure 6:
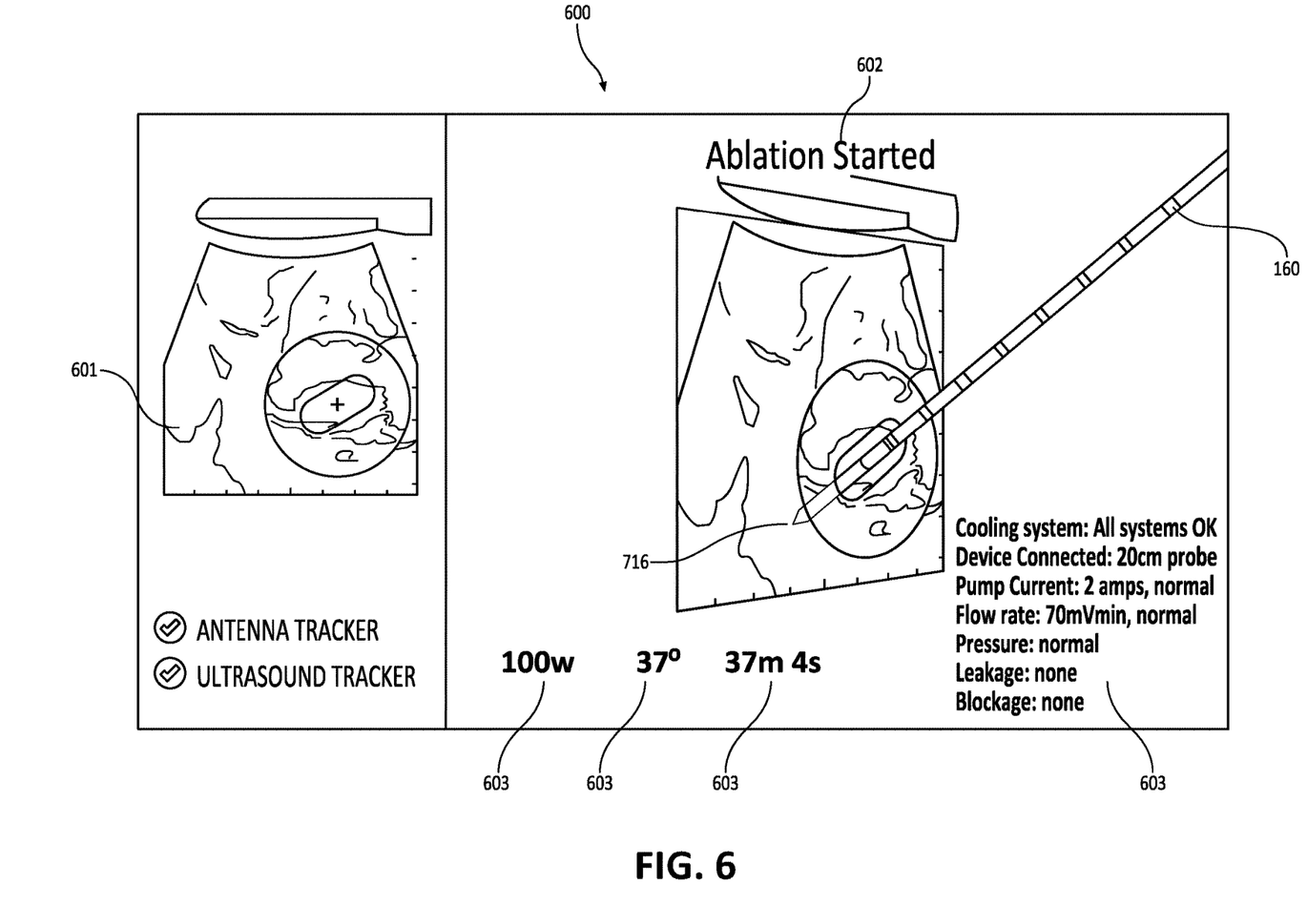
FIG. 6 is an illustration of a user interface presenting a view during a microwave ablation treatment in accordance with the present disclosure.

Application 216 may be one or more software programs stored in memory 102 and executed by processor 104 of computing device 100 or touch display computer 110. Referring also to FIG. 1, computing device 100 may be linked to touch display computer 110, thus enabling computing device 100 to control the output on and touch display computer 110 along with the output on second display 130. Computing device 100 may control touch display computer 110 to display output which is the same as or similar to the output displayed on second display 130. For example, the output on display 130 may be mirrored on touch display computer 110. Alternatively, as described above computing device 100 may control second display 130 to display different output from that displayed on touch display computer 110. For example, second display 130 may be controlled to display guidance images and information during the microwave ablation procedure, while touch display computer may display other output, such as configuration or status information see (FIG. 6).

Figure 3:
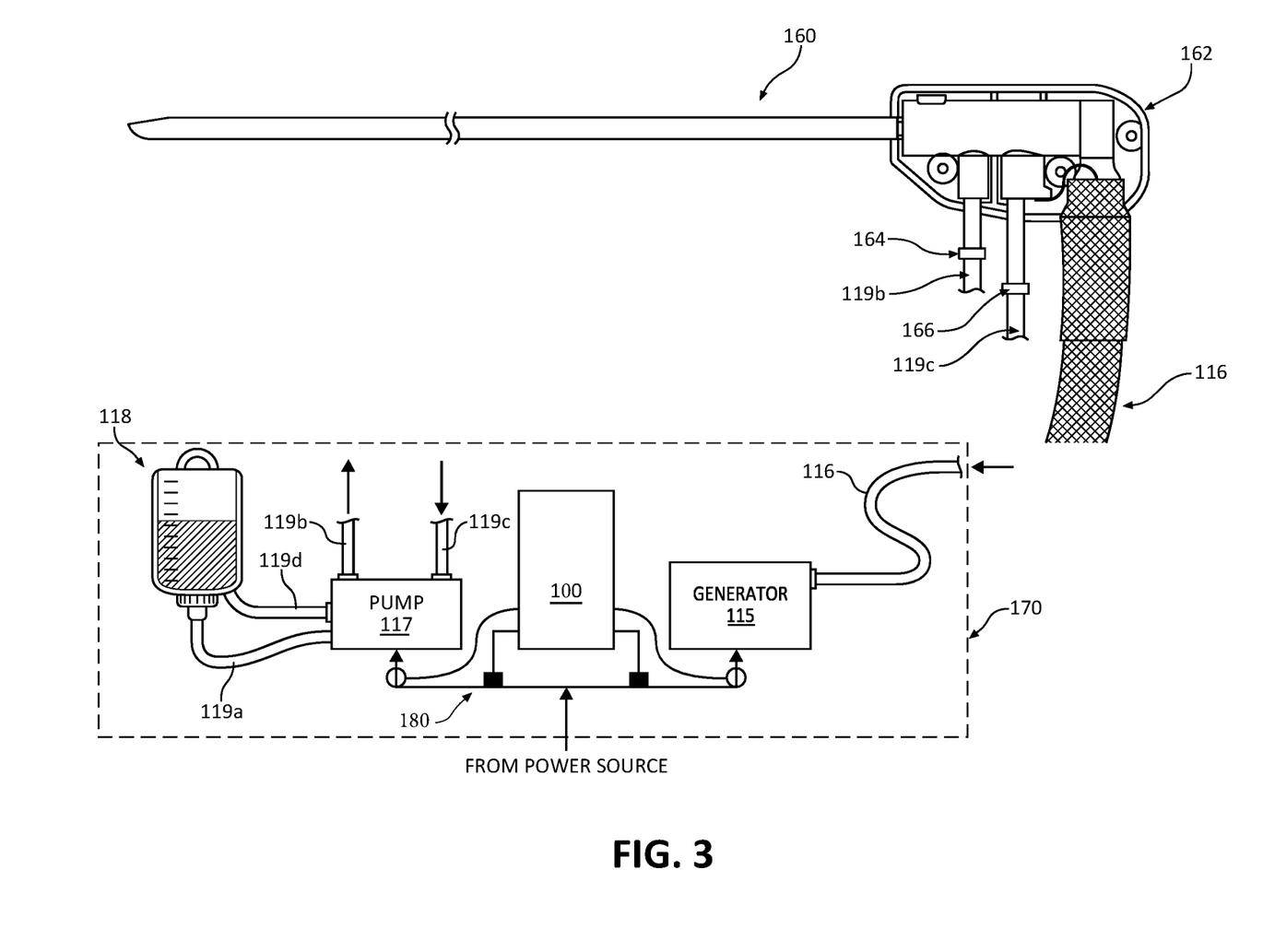
FIG. 3 is a side, partial cross-sectional view of a fluid cooled microwave ablation probe and base unit of the system of FIG. 1.

Referring now to FIG. 3, microwave ablation antenna assembly 160, microwave ablation generator 115, computing device 100, and peristaltic pump 117 are depicted schematically as housed on base unit 170 of system 10 (FIG. 1) are illustrated. Microwave ablation antenna assembly 160 is coupled to a microwave generator 115 via a flexible coaxial cable 116. Microwave generator 115 is configured to provide microwave energy at an operational frequency from about 915 MHz to about 2.45 GHz, although other suitable frequencies are also contemplated. Microwave ablation antenna assembly 160 may include a connection hub 162 for connection of coaxial cable 116, as well as the connection of a fluid inlet port 164 and a fluid outlet port 166. Fluid inlet port 164 permits the ingress of fluid into the microwave ablation antenna assembly 160 for cooling of components housed therein and control of the energy dissipation of microwave energy. Fluid outlet port 166 permits the egress of the fluid following circulation of the fluid through the microwave ablation antenna assembly 160.

The ports 164 and 166 are also coupled to a pump 117 that is, in turn, coupled to a supply tank 118 via a connection line 119a. Supply tank 118 may be a fluid filled bag (e.g., saline), as depicted in FIG. 3, or any other type of storage unit for any type of fluid. Pump 117 may be a positive displacement pump, such as a peristaltic pump. The supply tank 118 stores the fluid and may maintain the fluid at a predetermined temperature. The supply tank 118 may include a coolant unit (not explicitly shown) that cools returning liquid from the microwave ablation antenna assembly 160. In another embodiment, the fluid may be a gas and/or a mixture of liquid and gas. Pump 117 forces fluid from supply tank 118 through a supply line 119b into microwave ablation antenna assembly 160, such that heat is drawn away from the microwave ablation antenna assembly 160, which may enhance the overall ablation pattern, prevent damage to microwave ablation antenna assembly 160, and prevent harm to the clinician or patient. The fluid is returned to pump 117 and, ultimately, supply tank 118, via return line 119c and pump return line 119d.

Figure 4:
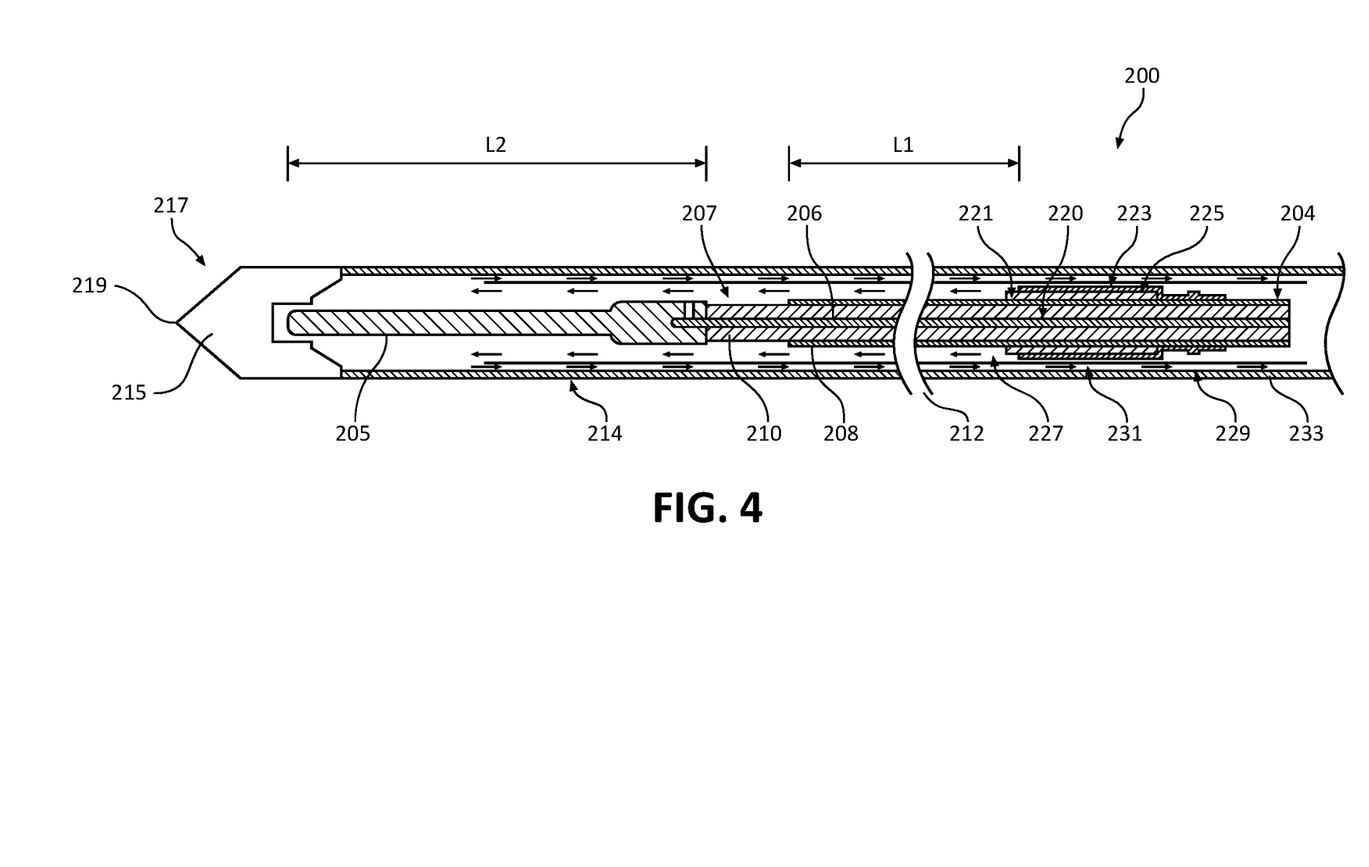
FIG. 4 is a cross-sectional view of a distal end of the ablation probe of FIG. 3.

FIG. 4 illustrates the distal portion 200 of the microwave ablation antenna assembly 160. Distal portion 200 of microwave ablation antenna assembly includes a proximal radiation portion 212 having a length "L1," and a distal radiation portion 214 having a length "L2," including an electrically-conductive radiator 205 and a feed point 207 disposed between the proximal and distal radiating portions 212 and 214. A feedline 204 is formed of a coaxial cable having an inner conductor 206, and outer conductor 208, and a dielectric 210 separating the two. The feedline 204 is connected at its proximal end to flexible cable 116 (FIG. 3). The distal radiating portion 214 and the proximal radiation portion 212 may be either balanced (e.g., of equal lengths) or unbalanced (e.g., of unequal lengths). The proximal radiating portion 212 may be formed of a portion of the feedline 204, and particularly the outer conductor 208 extending between a balun 220 and the feed point 207.

Referring still to FIG. 4, microwave ablation antenna assembly 160 also includes a balun (also called a choke) 220 disposed around the feedline 204. The balun 220 may be a quarter-wavelength balun formed of at least a dielectric layer 221 and a conductive layer 223. The conductive layer 223 may be shorted to the feedline 204 at the proximal end of the balun 220 by soldering or other suitable methods, or may be in electrical contact with a balun short 225 which itself is in electrical contact with the outer conductor 208 of the feedline 204. Microwave ablation antenna assembly 160 also includes a tip 215 having a tapered end 217 that terminates, in one embodiment, at a pointed end 219 to allow for insertion into tissue with minimal resistance. In cases where the microwave ablation assembly 160 is inserted into a pre-existing opening, tip 215 may be rounded or flat. The tip 215 may be formed from a variety of heat-resistant materials suitable for penetrating tissue, such as metals (e.g., stainless steel) and various thermoplastic materials, such as poletherimide, and polyamide thermoplastic resins.

The microwave ablation antenna assembly 160 includes fluid channels 227 and 229. Fluid channel 227 is spaced between the feedline 204 (including its electrically connected components balun 220 and proximal and distal radiating portions 212 and 214) and an inner tube 231. Fluid channel 229 is formed between the inner tube 231 and an outer cannula 233 of the microwave ablation antenna assembly 160. Fluid channel 227 connects to fluid inlet port 164 and fluid channel 229 connects to fluid outlet port 166, thereby completing a fluid circuit from the fluid tank 118, through the pump 117 and through the microwave antenna ablation assembly 160.

Referring back to FIG. 3, a power source provides power to base unit 170, while computing device 100 controls the operation of microwave generator 115 and peristaltic pump 117 of base unit 170. A current sensor 180 operably connected with computing device 110 computing device 100 measures the electrical current drawn by peristaltic pump 117 during operation thereof. Computing device 100 may then adjust energy output from generator 115 (or to microwave ablation antenna assembly 160) and/or the power supplied to peristaltic pump 117 (to thereby vary the rate at which pump 117 operates) based on the sensed electrical current drawn by peristaltic pump 117, as will be described in more detail below.

Figure 5:
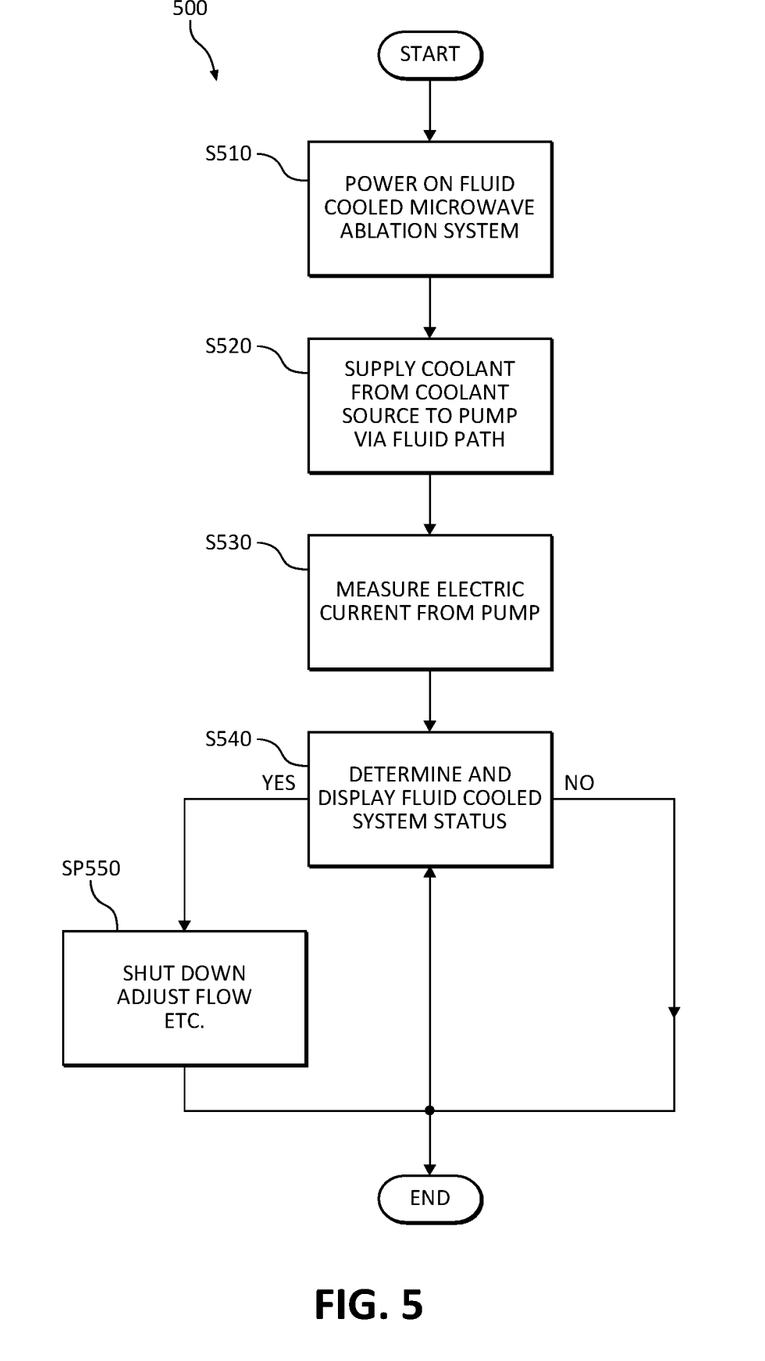
FIG. 5 is a flow chart illustrating a method of determining the status of a fluid cooled microwave ablation system in accordance with the present disclosure.

Referring now to FIG. 5, in conjunction with FIG. 3, a method 500 of determining the status of a fluid cooled treatment system is provided in accordance with the present disclosure. Although detailed with respect to fluid cooled microwave ablation system 10 (FIG. 1), method 500 may be used in conjunction with any other suitable fluid cooled treatment system. Method 500 may be implemented by a software program(s) or sub-program(s) loaded onto and/or integrated into application 216 of computing device 100.

Method 500 initially includes powering on the system 10 at S510. Powering on the system may include, for example, turning on computing device 100, base unit 170, and/or pump 117, selecting an application 216, using ultrasound workstation 150 to properly place microwave ablation antenna assembly 160 in the appropriate surgical site, and energizing microwave ablation antenna assembly 160 to emit microwave radiation therefrom for treating tissue therewith. Method 500 further includes, at S520, supplying fluid from a fluid supply to cool the system. More specifically, at S520, power from the power supply is drawn by pump 117 to pump fluid from fluid supply 118 to microwave ablation antenna assembly 160 via supply line 119*b*, and to return the fluid from microwave ablation antenna assembly 160 to fluid supply 118 via return line 119*c*. In embodiments, supplying fluid (S520) may alternatively be performed before or simultaneously with powering on the system (S510).

At S530, the electrical current drawn by pump 117 is measured. More specifically, current sensor 350 is utilized to measure the electrical current drawn by pump 117 from the power supply and to relay the same to computing device 100. Measuring the electrical current at S530 may be performed continuously or periodically, and may begin upon initiation of the supply of fluid (S520) or at any other suitable point during use.

Based upon the sensed electrical current (S530), the status of fluid cooled microwave ablation system 10 is determined at S540. Determining the status may include determining whether pump 117 is operating within established parameters (based upon the currently drawn by pump 117), which, in turn, may indicate whether system 10 is operating normally. If the electrical current drawn by pump 117 is outside normal operating parameters, computing device 100 may inhibit further operation of system 10, or provide an alert to a user, as such may indicate a problem, e.g., that there is an improper connection in supply line 119*b* or return line 119*c*, and/or that there is a blockage or leakage in the system 10.

Method 500, as detailed above, is utilized to determine the status of system 10 based upon the current drawn by the pump 117 thereof. This is based upon the fact that the current drawn by the pump 117 is indicative of the pressure and flow rate of the fluid being pumped through the system 10. More specifically, a greater electrical current draw by pump 117 is required to pump the fluid at an increased pressure and/or flow rate. Likewise, less electrical current drawn by pump 117 is needed to pump the fluid at a reduced pressure and/or flow rate. As such, electrical current drawn by pump 117 may be correlated to fluid flow rate and/or pressure, and, thus, may be a useful in determining the status of system 10.

For example, an increased current draw may indicate increased pressure, which may be the result of a blockage (or partial blockage) within the system 10. The blockage may be the result of a person (e.g., clinician) unintentionally standing and/or sitting on supply line 119*b* or return line 119*c* or an object being disposed within, on, or over supply line 119*b* or return line 119*c* thereby inhibiting flow therethrough. A decreased current draw may indicate reduced pressure, which may be the result of a faulty connection, leakage, or lack of fluid within the system 10. As can be appreciated in view of the above, by monitoring the electrical current drawn by pump 117, damage to the system 10 as well as harm to the clinician or patient may be prevented. Monitoring the electrical current drawn by pump 117 may be more advantageous than, for example, monitoring temperature from a temperature sensor on microwave ablation antenna assembly 160, because, while useful, temperature may be a lagging indicator of a problem whereas pump current draw is a leading indicator that there may be an immediate issue within system 10.

Computing device 100 may continually monitor, record, measure, determine and/or display the electrical current drawn by pump 117 at any and all times before and/or during a procedure. Upon determining that the electrical current drawn by pump 117 is outside normal operating parameters, computing device 100 may inhibit further operation of system 10 or provide an alert to a user, warning of a potentially unsafe condition. The alert may be in the form of visual, audible, and/or tactile feedback (FIG. 6, described in more detail below).

Referring still to FIGS. 3 and 5, computing device 100 may store normal operating range data of the current drawn by the pump 117 when used with system 10 and, during use, compare this range to the sensed data from current sensor 180 to determine if system 10 is operating normally. This data may be determined experimentally, empirically based upon the components utilized, or in any other suitable manner. In embodiments, manufacturer performance data for pump 117 (e.g., performance curves) and any or all of the other components of system 10, e.g., microwave ablation antenna assembly 160, the tubing (lines 119*b*, 119*c*), the fluid supply 118, the particular fluid, etc., may be input into computing device 100 and/or application 216. Such data may be used to calculate the normal operating range data for that particular system 10 set-up. Computing device 100 may compare this normal operating range data to real time data (determined by computing device 100 using current sensor 180) to determine if the real-time data falls within, above, or below the normal operating range. Should the real time data fall outside the acceptable ranges, a blockage, leakage, or other problem (e.g., tubing not properly placed in pump head, pump head door not closed, incompatible pump tubing used with system, defective pump tubing used with system, etc.) in the system 10 may be present which causes the pump 117 to need to work harder or not as hard (as reflected by the current drawn by the pump 117).

Computing device 100 may also make calculations and/or determinations based on the specifications of the pump 117 used in fluid cooled treatment system 10. For example, if pump 117 is a peristaltic pump, then computing device may calculate flow rate based on peristaltic pump's 117 tube inner diameter(s), outer diameter(s), pump head RPM, or occlusion, which computing device 100 may then compare to the electrical current data from pump 117, such that the status of fluid cooled treatment system 10 may be determined.

In an embodiment, computing device 100 may be able to determine and display (FIG. 6) the type of ablation probe being used during the procedure. Since each type of ablation probe is rated for a specific electrical current usage (e.g., watts), computing device 100 may determine the type of device that is connected to fluid cooled treatment system 10 by using the electrical current profile of microwave ablation antenna assembly 160 as a metric. For example, touch display computer 110 (FIG. 6) may indicate whether the microwave ablation antenna assembly 160 connected to fluid cooled treatment system 10 is a short length (15 cm), standard length (20 cm), or long length (30 cm), each of which have unique electrical current profiles e.g., that are specific to the length of their respective probes.

With continued reference to FIG. 5, a safety protocol SP550 may be implemented with method 500 to prevent an unsafe condition to the clinician or patient. Safety protocol SP550 of computing device 100 may compare the electrical current drawn by pump 117 to a known, safe range. With safety protocol SP550 in use, electrical current data by pump 117 is provided to computing device 100, which may represent a real-time measurement. If the electrical current drawn by pump 117 is within a predetermined range (normal operating range), computing device 100 may control the fluid cooled treatment 10 to continue with the ablation procedure. If the electrical current is outside the predetermined range, safety protocol SP550 of computing device 100 may implement an interlock to cease the ablation procedure, provide an alert, and/or modify the operation of microwave generator 115 and/or pump 117.

Moreover, if the temperature of microwave antenna assembly 160 is out of a normal range, fluid cooled treatment system 10 and/or computing device 100 may adjust the electrical current to pump 117 to maintain the temperature within a normal range. As such, the current of pump 117 and temperature feedback of microwave ablation antenna assembly 160 may be used to avoid an overshoot and/or undershoot of both flow rate and device temperature. The power level of microwave generator 115 may also be automatically adjusted based on the temperature of microwave ablation antenna assembly 160 and electrical current drawn from pump 117. All of the aforementioned systems may be interdependent and managed to maintain a desirable system state. In addition, the supplying of energy to microwave ablation antenna assembly 160 may be delayed until coolant from fluid cooled treatment system 10 has been primed, such that an unsafe condition may be avoided. The predetermined range of electrical current drawn by pump 117 may correspond to a normal range of fluid flow rates and/or pressures through supply line 119b (FIG. 3), return line 119c (FIG. 3) provided in application 216 of computing device 100.

Referring now to FIG. 6, an example screen 600, which may be displayed on touch display computer 110 or display 130 during a microwave ablation procedure, is shown. Screen 600 includes a view 601 of the live 2D ultrasound images captured during the procedure. Screen 600 further includes a view 602 for showing transient messages relating to the ablation procedure. Screen 600 may include a view 603 for displaying status messages relating to electrical current drawn by pump 117, which, as detailed above, may be indicative of leakages, blockages, or other system problems. By way of another example, view 603 may indicate whether fluid cooled treatment system 10 is operating normally. View 603 may also display other useful information, such as the temperature, elapsed time of the procedure, and the output from the electrosurgical generator (indicated here in watts).

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An ablation system, comprising:
an ablation probe defining a fluid path for circulation of a fluid therethrough and having tubing in fluid communication with the fluid path;
a generator configured to supply energy to the ablation probe for treating a tissue;
a pump configured to operably couple to the tubing and to pump the fluid through the fluid path of the ablation probe to cool the ablation probe;
a sensor configured to measure an electrical current drawn by the pump; and
a computing device configured to:
store, in a memory, performance data for the tubing operably coupled to the pump and performance data for the fluid pumped through the fluid path by the pump;
calculate a normal electrical current operating range for the pump based on the stored performance data for the tubing operably coupled to the pump and the stored performance data for the fluid pumped through the fluid path by the pump;
determine at least one of a flow rate or a pressure of the fluid pumped through the fluid path by the pump based on the measured electrical current;
determine that an occlusion along the fluid path exists when the measured electrical current is above the calculated normal electrical current operating range for the pump;
determine that a leakage along the fluid path exists when the measured electrical current is below the calculated normal electrical current operating range for the pump; and
display an indication of whether the occlusion along the fluid path exists and an indication of whether the leakage along the fluid path exists.

2. The system according to claim 1, wherein the computing device is further configured to inhibit the pump from pumping the fluid through the ablation probe if the measured electrical current is outside the calculated normal electrical current operating range for the pump.

3. The system according to claim 1, wherein the computing device is further configured to inhibit the supply of the energy from the generator to the ablation probe if the measured electrical current is outside the calculated normal electrical current operating range for the pump.

4. The system according to claim 1, wherein the computing device is further configured to provide an alert if the measured electrical current is outside the calculated normal electrical current operating range for the pump.

5. The system according to claim 4, further comprising a display screen configured to display the alert.

6. The system according to claim 5, wherein the display screen is further configured to display the measured electrical current.

7. The system according to claim 1, wherein the fluid path includes:
an inflow path in fluid communication with a fluid supply conduit of the pump, the inflow path defined between a feedline of the ablation probe and an inner tube of the ablation probe coaxially disposed around the feedline; and an outflow path in fluid communication with a fluid return conduit of the pump, the outflow path defined between the inner tube and an outer cannula of the ablation probe.

8. The system according to claim 7, wherein the ablation probe includes a balun coupled to the feedline and disposed within the inflow path.

9. The system according to claim 1, further comprising a power source operably coupled to the pump and configured to deliver the electrical current to the pump.

10. The system according to claim 9, wherein the sensor is disposed between the power source and the pump.

11. The system according to claim 1, wherein the computing device is separate from the pump.

12. The system according to claim 1, wherein the computing device is separate from the generator.

13. The system according to claim 1, wherein the computing device is further configured to calculate the normal electrical current operating range for the pump based on performance data for the ablation probe.

14. An ablation system, comprising:
an ablation probe defining a fluid path for circulation of a fluid therethrough and having tubing in fluid communication with the fluid path;
a microwave generator configured to supply microwave energy to the ablation probe for treating a tissue;
a fluid pump configured to operably couple to the tubing and to pump the fluid through the fluid path of the ablation probe to cool the ablation probe;
a power supply configured to deliver an electrical current to the fluid pump;
a current sensor disposed between the power supply and the fluid pump and configured to measure the electrical current drawn from the power supply by the fluid pump; and
a computing device configured to:
store, in a memory, performance data for the tubing operably coupled to the fluid pump and performance data for the fluid pumped through the fluid path by the fluid pump;
calculate a normal electrical current operating range for the fluid pump based on the stored performance data for the tubing operably coupled to the fluid pump and the stored performance data for the fluid pumped through the fluid path by the fluid pump;
determine a flow rate of the fluid pumped through the fluid path by the fluid pump based on the measured electrical current drawn by the fluid pump from the power supply;
determine that an occlusion along the fluid path exists when the measured electrical current drawn by the fluid pump is above the calculated normal electrical current operating range for the fluid pump;
determine that a leakage along the fluid path exists when the measured electrical current drawn by the fluid pump is below the calculated normal electrical current operating range for the fluid pump; and display an indication of whether the occlusion along the fluid path exists and an indication of whether the leakage along the fluid path exists.

15. The system according to claim 14, wherein the fluid path includes:
an inflow path in fluid communication with a fluid supply conduit of the fluid pump, the inflow path defined between a feedline of the ablation probe and an inner tube of the ablation probe coaxially disposed around the feedline; and
an outflow path in fluid communication with a fluid return conduit of the fluid pump, the outflow path defined between the inner tube and an outer cannula of the ablation probe.

16. The system according to claim 15, wherein the ablation probe includes a balun coupled to the feedline and disposed within the inflow path.

17. The system according to claim 14, wherein the computing device is further configured to calculate the normal electrical current operating range for the fluid pump based on performance data for the ablation probe.

18. An ablation system, comprising:
an ablation probe defining a fluid path for circulation of a fluid therethrough and having tubing in fluid communication with the fluid path;
a pump configured to operably couple to the tubing and to pump the fluid through the fluid path of the ablation probe to cool the ablation probe;
a sensor configured to measure an electrical current drawn by the pump; and
a computing device configured to:
store, in a memory, performance data for the tubing operably coupled to the pump and performance data for the fluid pumped through the fluid path by the pump;
calculate a normal electrical current operating range for the pump based on the stored performance data for the tubing operably coupled to the pump and the stored performance data for the fluid pumped through the fluid path by the pump; determine at least one of a flow rate or a pressure of the fluid pumped through the fluid path by the pump based on the measured electrical current; determine that an occlusion along the fluid path exists when the measured electrical current is above the calculated normal electrical current operating range for the pump; determine that a leakage along the fluid path exists when the measured electrical current is below the calculated normal electrical current operating range for the pump; and display an indication of whether the occlusion along the fluid path exists and an indication of whether the leakage along the fluid path exists.

19. The system according to claim 18, wherein the computing device is further configured to calculate the normal electrical current operating range for the pump based on performance data for the ablation probe.

\* \* \* \* \*